United States Patent
Liu et al.

(10) Patent No.: US 12,004,284 B2
(45) Date of Patent: Jun. 4, 2024

(54) METHODS AND SYSTEMS FOR X-RAY IMAGING

(71) Applicant: GE Precision Healthcare LLC, Milwaukee, WI (US)

(72) Inventors: James Z. Liu, Salt Lake City, UT (US); Russell Dibb, Salt Lake City, UT (US); Naveen S. Chandra, Salt Lake City, UT (US)

(73) Assignee: GE Precision Healthcare LLC, Milwaukee, WI (US)

( * ) Notice: Subject to any disclaimer, the term of this patent is extended or adjusted under 35 U.S.C. 154(b) by 296 days.

(21) Appl. No.: 17/451,789

(22) Filed: Oct. 21, 2021

(65) Prior Publication Data

US 2023/0126216 A1 Apr. 27, 2023

(51) Int. Cl.
*H05G 1/04* (2006.01)
*A61B 6/00* (2006.01)
(Continued)

(52) U.S. Cl.
CPC ............. *H05G 1/04* (2013.01); *A61B 6/4441* (2013.01); *H05G 1/265* (2013.01); *H05G 1/34* (2013.01); *H01J 35/16* (2013.01)

(58) Field of Classification Search
CPC ....... A61B 6/405; A61B 6/4085; A61B 6/542; A61B 6/488; A61B 6/4441; A61B 6/54; A61B 6/56; A61B 6/4405; A61B 6/032; A61B 6/4014; A61B 6/4241; A61B 6/482; A61B 6/5205; A61B 6/544; A61B 6/545; A61B 6/027; A61B 6/0407; A61B 6/0457;
(Continued)

(56) References Cited

U.S. PATENT DOCUMENTS 6,373,915 B1 4/2002 Fujimoto
6,574,493 B2 6/2003 Rasche et al.
(Continued)

FOREIGN PATENT DOCUMENTS

JP 2014230707 A 12/2014

OTHER PUBLICATIONS

Sheth, N. et al., "A mobile isocentric C-arm intraoperative cone-beam CT: Technical assessment of dose and 3D imaging performance," Medical Physics, vol. 47, No. 3, Dec. 2019, 17 pages.
(Continued)

*Primary Examiner* — Irakli Kiknadze

(57) ABSTRACT

Various methods and systems are provided for medical imaging systems. In one example, an imaging system comprises: a C-shaped gantry; an x-ray tube coupled to a first end of the C-shaped gantry; an x-ray detector coupled to a second end of the C-shaped gantry, opposite to the x-ray tube; and a controller with computer readable instructions stored on non-transitory memory that when executed, cause the controller to: identify a reference image; determine a target electrical current based on the reference image; determine a corrected electrical current based on the target electrical current; and transition an electrical current provided to the x-ray tube to the target electrical current by commanding the electrical current to the corrected electrical current while maintaining a constant voltage provided to the x-ray tube.

16 Claims, 4 Drawing Sheets

(51) Int. Cl.
*H01J 35/16* (2006.01)
*H05G 1/26* (2006.01)
*H05G 1/34* (2006.01)

(58) Field of Classification Search
CPC ....... A61B 6/0487; A61B 6/461; A61B 6/469; A61B 6/483; A61B 6/5282; A61B 6/03; A61B 6/463; A61B 6/583; H05G 1/265; H05G 1/34; H05G 1/04; H01J 35/16; G01N 2223/423; G01N 23/046; G06T 11/008; G06T 2211/408; G06T 11/005; G06T 2207/10081; G06T 2211/444
USPC ......... 378/4, 15, 62, 109–118, 193, 196–198
See application file for complete search history.

(56) References Cited

U.S. PATENT DOCUMENTS

| | | |
|---|---|---|
| 6,666,579 B2 | 12/2003 | Jensen |
| 7,197,105 B2 | 3/2007 | Katsevich |
| 7,597,477 B1 | 10/2009 | Hosseinian et al. |
| 7,778,392 B1 | 8/2010 | Berman et al. |
| 7,856,080 B2 | 12/2010 | Klingenbeck-Regn |
| 7,856,084 B2 | 12/2010 | Pasini et al. |
| 8,107,592 B2 | 1/2012 | Berman et al. |
| 8,213,565 B2 | 7/2012 | Boese et al. |
| 8,249,213 B2 | 8/2012 | Noordhoek et al. |
| 8,285,014 B2 | 10/2012 | Lauritsch et al. |
| 8,447,009 B2 | 5/2013 | Flohr et al. |
| 8,494,245 B2 | 7/2013 | Liao et al. |
| 8,644,576 B2 | 2/2014 | Zheng et al. |
| 8,724,881 B2 | 5/2014 | Zheng et al. |
| 8,781,243 B2 | 7/2014 | Chen et al. |
| 8,934,693 B2 | 1/2015 | Grbic et al. |
| 9,076,237 B2 | 7/2015 | Chen et al. |
| 9,292,917 B2 | 5/2016 | Grbic et al. |
| 9,373,159 B2 | 6/2016 | Amroabadi et al. |
| 9,384,546 B2 | 7/2016 | Zheng et al. |
| 9,414,799 B2 | 8/2016 | Mistretta et al. |
| 10,417,765 B2 | 9/2019 | Saalbach et al. |
| 10,492,751 B2 | 12/2019 | Miao et al. |
| 10,582,905 B2 | 3/2020 | Liu et al. |
| 2001/0034480 A1 | 10/2001 | Rasche et al. |
| 2002/0085681 A1 | 7/2002 | Jensen |
| 2006/0034417 A1 | 2/2006 | Katsevich |
| 2008/0247503 A1 | 10/2008 | Lauritsch et al. |
| 2009/0076373 A1 | 3/2009 | Maschke |
| 2009/0161821 A1 | 6/2009 | Klingenbeck-Regn |
| 2009/0198121 A1 | 8/2009 | Hoheisel |
| 2009/0281452 A1 | 11/2009 | Pfister et al. |
| 2010/0036239 A1 | 2/2010 | Klingenbeck-Regn |
| 2010/0272342 A1 | 10/2010 | Berman et al. |
| 2011/0075798 A1 | 3/2011 | Boese et al. |
| 2011/0135053 A1 | 6/2011 | Noordhoek et al. |
| 2011/0222750 A1 | 9/2011 | Liao et al. |
| 2012/0014500 A1 | 1/2012 | Flohr et al. |
| 2012/0177267 A1 | 7/2012 | Chen et al. |
| 2012/0230570 A1 | 9/2012 | Zheng et al. |
| 2013/0046176 A1 | 2/2013 | Mistretta et al. |
| 2013/0129170 A1 | 5/2013 | Zheng et al. |
| 2013/0129173 A1 | 5/2013 | Grbic et al. |
| 2013/0129174 A1 | 5/2013 | Grbic et al. |
| 2013/0294667 A1 | 11/2013 | Zheng et al. |
| 2014/0270454 A1 | 9/2014 | Chen et al. |
| 2015/0038862 A1 | 2/2015 | Gijscers et al. |
| 2015/0187052 A1 | 7/2015 | Amroabadi et al. |
| 2015/0282779 A1 | 10/2015 | Deuerling-Zheng et al. |
| 2015/0320381 A1* | 11/2015 | Kobayashi ............. A61B 6/542 378/68 |
| 2017/0179186 A1* | 6/2017 | Jacob ................... G01N 23/043 |
| 2017/0215818 A1 | 8/2017 | De Man et al. |
| 2017/0365059 A1 | 12/2017 | Saalbach et al. |
| 2018/0049714 A1* | 2/2018 | Nett ....................... A61B 6/542 |
| 2019/0231296 A1* | 8/2019 | Jackson ................. A61B 6/488 |
| 2020/0242783 A1* | 7/2020 | Lauritsch .............. G06T 11/008 |

OTHER PUBLICATIONS

"ZIEHM Vision RFD 3D.," ZIEHM Website, Available Online at https://www.ziehm.com/en/us/products/c-arms-with-flat-panel-detector/ziehm-vision-rfd-3d.html, Available as Early as Aug. 8, 2020, 7 pages.

"Siemens ARCADIS Orbic 3D," Soma Technology Website, Available Online at https://www.somatechnology.com/C-Arms/Siemens-ARCADIS-Orbic-3D.aspx, Available as Early as Oct. 27, 2020, 3 pages.

"Ziehm Vision (FD) Vario 3D Exceptional 2D and 3D imaging with smallest footprint," Ziehm Website, Available Online at https://www.ziehm.com/fileadmin/user_upload/row/02-products/ziehm-vision-fd-vario-3d/ziehm-vision-vario-3d-and- ziehm-vision-fd-vario-3d-product-brochure.pdf, Retrieved on Oct. 21, 2021, 20 pages.

"SIREMOBIL Iso-C3D-Breathtaking Views in the OR!," Meditegic Website, Available Online at https://www.meditegic.com/wp-content/uploads/pdfs/SIEMENS_ICO-C3D.PDF, Retrieved on Oct. 21, 2021, 16 pages.

"Workflow simplification with XperCT: Relief of complications due to spontaneous gastric perforation," Philips Website, Available Online at https://www.documents.philips.com/assets/20170523/d0e783949a5b4ad08780a77c0158de95.pdf, Retrieved on Oct. 21, 2021, 4 pages.

* cited by examiner

METHODS AND SYSTEMS FOR X-RAY IMAGING

FIELD

Embodiments of the subject matter disclosed herein relate to medical imaging systems, and more particularly, to radiographic imaging systems.

BACKGROUND

Radiographic imaging systems may be used in various applications, including medical and industrial applications. In a medical environment, a radiographic imaging device may provide a non-invasive means of imaging tissue and bone of a patient. The imaging device may have the capability of capturing multiple images at designated intervals and displaying the images in a sequence to create a single image of the object being examined.

The imaging device may comprise a C-arm coupled to a base unit. The C-arm may include an x-ray source positioned at one end of the arm and a detector positioned at another end of the arm. A clearance may be provided between the x-ray source and the detector to receive an object, such as a portion of the patient's body, which may be irradiated with radiation from the x-ray source. Upon irradiating the object, the x-ray radiation penetrates through the object and is captured by the detector. By penetrating the object placed between the source and detector, the x-rays enable an image of the object to be captured and relayed to the display monitor, where the image may be displayed or stored and retrieved later.

BRIEF DESCRIPTION

In one example, an imaging system comprises: a C-shaped gantry; an x-ray tube coupled to a first end of the C-shaped gantry; an x-ray detector coupled to a second end of the C-shaped gantry, opposite to the x-ray tube; and a controller with computer readable instructions stored on non-transitory memory that when executed, cause the controller to: identify a reference image; determine a target electrical current based on the reference image; determine a corrected electrical current based on the target electrical current; and transition an electrical current provided to the x-ray tube to the target electrical current by commanding the electrical current to the corrected electrical current while maintaining a constant voltage provided to the x-ray tube.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figures 3, 4:
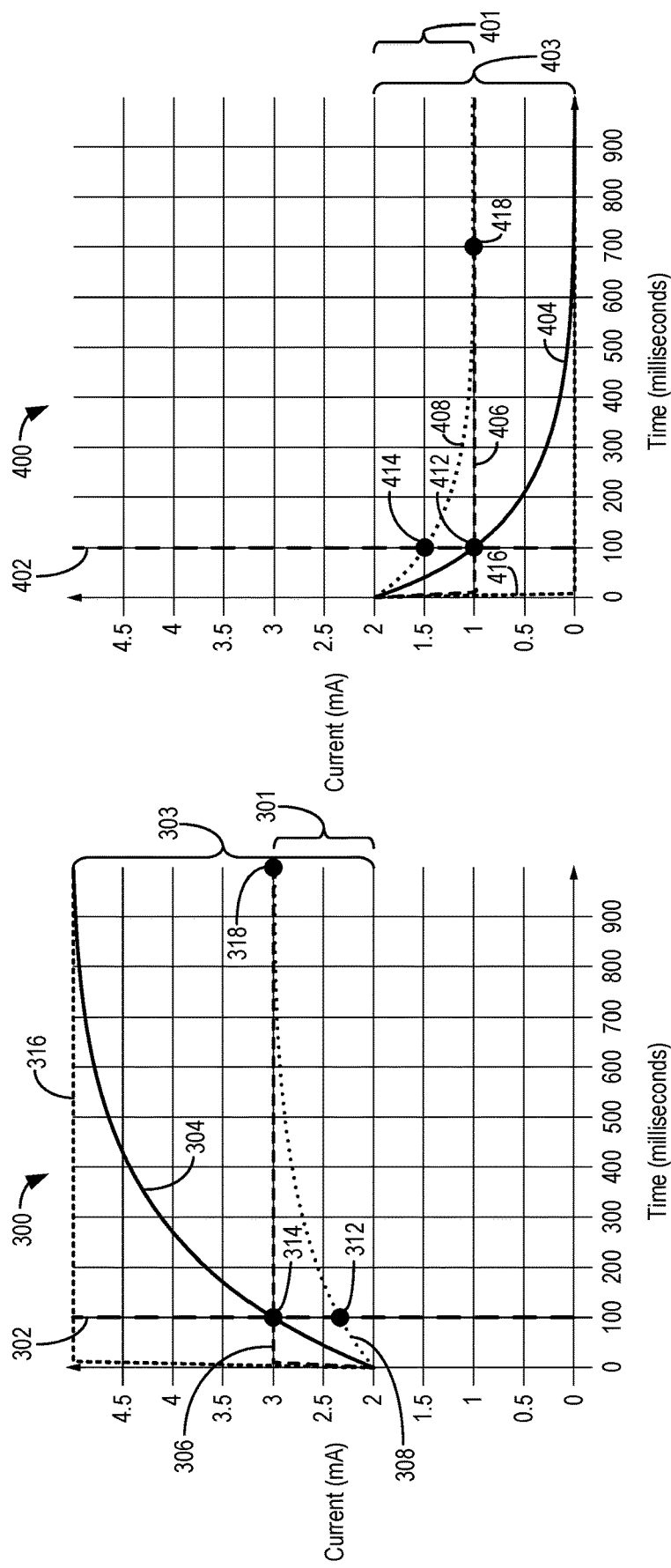
FIGS. 3-4 show different graphs with plots illustrating an electrical current of an x-ray tube of a medical imaging system and a commanded corrected electrical current, according to an embodiment.
Figure 5:
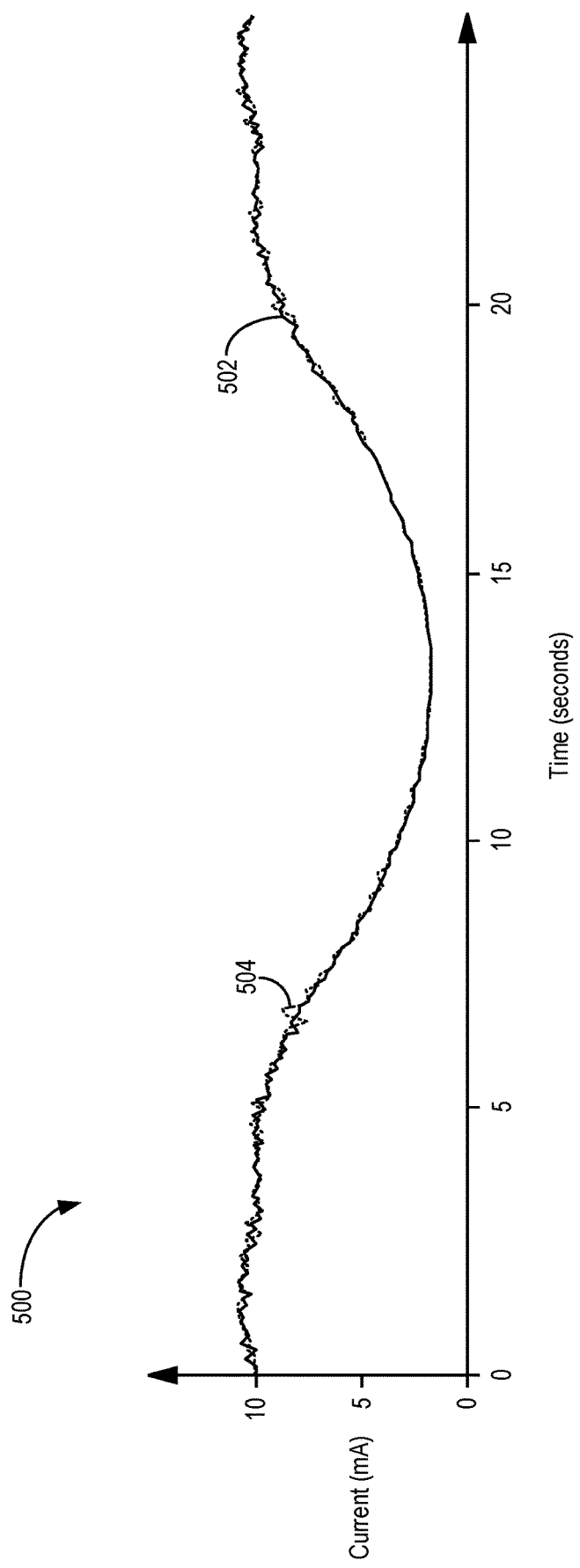
FIG. 5 shows a graph with plots illustrating an electrical current of an x-ray tube of a medical imaging system and a commanded corrected electrical current, according to an embodiment.

The following description relates to various embodiments for medical imaging systems and methods for controlling medical imaging systems. A 3D mobile C-arm imaging system is provided according to the present disclosure. Additionally, a control routine for a 3D mobile C-arm imaging system is provided according to the present disclosure. A medical imaging system, such as the medical imaging system shown by FIG. 1, includes a C-arm. A radiation source is arranged at a first end of the C-arm and a radiation detector is arranged at an opposing, second end of the C-arm. A subject to be imaged by the medical imaging system may be arranged between the radiation source and the radiation detector. The radiation source may emit radiation, such as x-ray radiation, and the radiation may pass through the subject, with attenuated x-ray radiation that has passed through the subject intercepted, or received, by the detector. An electrical current provided to the radiation source is controlled by an electronic controller of the imaging system. The controller may adjust the actual electrical current to a target electrical current having a desired value by commanding the electrical current to a corrected electrical current based on imaging parameters, according to the method illustrated by the flowchart of FIG. 2. The corrected electrical current may be offset from the target electrical current, as shown by FIGS. 3-4, to provide a transition of the actual electrical current to the target electrical current within a desired timeframe, such as a commanded transition duration between acquisition of sequential images. As a result, during a scan of a subject, the actual electrical current may be more responsively adjusted (e.g., matched) to the target electrical current, as shown by FIG. 5.

Figure 1:
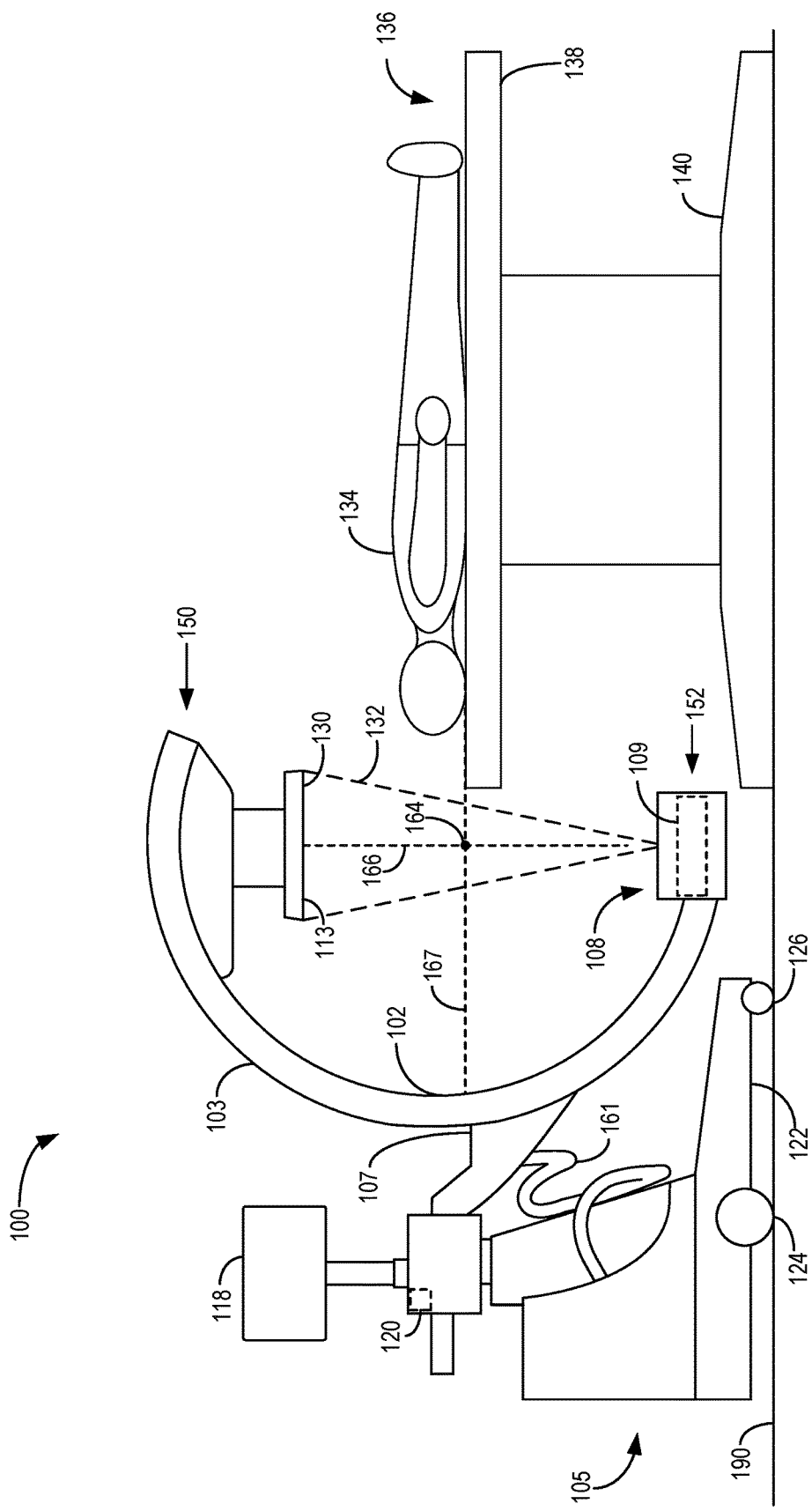
FIG. 1 shows an example medical imaging system including a C-arm, according to an embodiment.

Referring to FIG. 1, an imaging system 100 including a C-arm 102 (which may be referred to herein as a C-shaped gantry) is schematically shown. Imaging system 100 may be referred to herein as a medical imaging system and/or C-arm imaging system. The imaging system 100 includes a radiation source, and in the examples described herein, the radiation source is an x-ray unit 108 (which may be referred to herein as an x-ray tube) positioned opposite to detector 130 (which may be referred to herein as an x-ray detector) and configured to emit x-ray radiation. In other examples, the radiation source may be configured to emit a different type of radiation for imaging (e.g., imaging a subject, such as patient 134), such as gamma rays, and the detector (e.g., x-ray detector 130) may be configured to detect the radiation emitted by the radiation source (e.g., x-ray beam 132). The imaging system 100 additionally includes base unit 105 supporting imaging system 100 on ground surface 190 on which the imaging system 100 sits (e.g., via base 122 supported by wheel 124, wheel 126, etc.).

The C-arm 102 includes a C-shaped portion 103 connected to an extended portion 107, with the extended portion 107 rotatably coupled to the base unit 105. The detector 130 is coupled to the C-shaped portion 103 at a first end 150 of the C-shaped portion 103, and the x-ray unit 108 is coupled to the C-shaped portion 103 at an opposing, second end 152 of the C-shaped portion 103. As an example, the C-arm 102 may be configured to rotate at least 180 degrees in opposing directions relative to the base unit 105. The C-arm 102 is rotatable about at least a rotational axis 164 and may additionally rotate about axis 167. The C-shaped portion 103 may be rotated as described above in order to adjust the x-ray unit 108 and detector 130 (positioned on opposite ends of the C-shaped portion of the C-arm 102 along axis 166, where axis 166 intersects rotational axis 164 and extends radially relative to rotational axis 164) through a plurality of positions.

During an imaging operation (e.g., a scan), a portion of a patient's body placed in an opening formed between the x-ray unit 108 and detector 130 may be irradiated with radiation from the x-ray unit 108. For example, patient 134 may be supported by a patient support table 136, with the patient support table 136 including a support surface 138 and base 140, and may be arranged between the x-ray unit 108 and the detector 130. The x-ray unit 108 includes an x-ray tube insert 109 and x-ray radiation generated by the x-ray tube insert 109 may emit from the x-ray unit 108. The radiation may penetrate the portion of the patient's body arranged to be irradiated and may travel to the detector 130 where the radiation is captured (e.g., intercepted by a detector surface 113 of the detector 130). By penetrating the portion of the patient's body placed between the x-ray unit 108 and detector 130, an image of the patient's body is captured and relayed to an electronic controller 120 of the imaging system 100 (e.g., via an electrical connection line, such as electrically conductive cable 161). The image may be displayed via display device 118. Images of the subject acquired by the imaging system 100 via the x-ray unit 108 and the detector 130 as described above may be referred to herein as projection images and/or scan projection images.

The base unit 105 may include the electronic controller (e.g., a control and computing unit) that processes instructions or commands sent from the user input devices during operation of the imaging system 100. The base unit 105 may also include an internal power source (not shown) that provides electrical power to operate the imaging system 100. Alternatively, the base unit 105 may be connected to an external electrical power source to power the imaging system 100. A plurality of connection lines (e.g., electrical cables, such as electrically conductive cable 161) may be provided to transmit electrical power, instructions, and/or data between the x-ray unit 108, detector 130, and the control and computing unit. The plurality of connection lines may transmit electrical power from the electrical power source (e.g., internal and/or external source) to the x-ray unit 108 and detector 130.

The C-arm 102 may be adjusted to a plurality of different positions by rotation of the C-shaped portion 103 of the C-arm 102. For example, in an initial, first position shown by FIG. 1, the detector 130 may be positioned vertically above the x-ray unit 108 relative to a ground surface 190 on which the imaging system 100 sits, with axis 166 arranged normal to the ground surface 190 intersecting a midpoint of each of the outlet 111 of x-ray unit 108 and detector surface 113 of detector 130. The C-arm 102 may be adjusted from the first position to a different, second position by rotating the C-shaped portion 103. In one example, the second position may be a position in which the x-ray unit 108 and detector 130 are rotated 180 degrees together relative to the first position, such that the x-ray unit 108 is positioned vertically above the detector 130, with axis 166 intersecting the midpoint of the outlet 111 of the x-ray unit 108 and the midpoint of the detector surface 113 of the detector 130. When adjusted to the second position, the x-ray unit 108 may be positioned vertically above the rotational axis 164 of the C-shaped portion 103 of the C-arm 102, and the detector 130 may be positioned vertically below the rotational axis 164. Different rotational positions of the C-arm 102 are possible.

Detector saturation in cone-beam computed tomography (CBCT) refers to overexposure or over-range of images acquired by the computed tomography imaging system. During conditions in which detector saturation occurs, an intensity range of x-ray radiation is greater than the detector's detectable range in at least some projections. As a result, a loss of information occurs in the saturated area of the projection images, which may increase a likelihood of imaging artifacts, a loss of skin-line, a degradation of CT number accuracy, a reduction in a contrast-to-noise ratio of the acquired images, and/or image uniformity.

The dynamic range of an x-ray detector in a mobile C-arm system is often much smaller than the dynamic range of an x-ray detector in a traditional CT system (e.g., a stationary CT imaging system without a C-arm). In mobile C-arm systems, detector saturation may occur as imaging conditions change from one projection to the another due to varying thickness of the anatomy imaged. As a result, image quality may be degraded. Additionally, the x-ray detector of mobile C-arm systems is often a CMOS x-ray detector, which may provide lower electronic noise, lower electromagnetic interference, lower latency, faster reading, lower power consumption, less variation in operation due to temperature, etc. However, CMOS x-ray detectors have a dynamic range of approximately $\frac{1}{10}$ of the dynamic range of an amorphous silicon-based x-ray detector, which may increase a likelihood of detector saturation.

In mobile C-arm systems, a cathode-anode voltage of an x-ray tube (e.g., a voltage provided at an x-ray tube insert, such as x-ray tube insert 109) is often expressed as a kilovoltage peak (kVp). A duration to adjust the cathode-anode voltage of the x-ray tube to a commanded value (e.g., a commanded kVp) is often within a range of a few milliseconds. An electrical current applied to the x-ray tube is often expressed in milliamperes (mA), and electrical current may be referred to herein as mA. A duration to adjust the electrical current (e.g., adjust the mA), however, is much longer than the duration to adjust the cathode-anode voltage. Often, the duration to adjust the electrical current is approximately one second. Because the duration to adjust the cathode-anode voltage is much smaller than the duration to adjust the electrical current, adjusting the imaging parameters during a 3D scan in conventional imaging systems is often accomplished by mainly adjusting the voltage (kVp) instead of the current (mA). However, while adjusting the voltage during a scan, the x-ray attenuation and the CT number of a given voxel may vary from projection to projection as the voltage varies. The variation of the x-ray attenuation may reduce the accuracy of the CT number and may additionally increase a likelihood of image artifacts.

In order to reduce a likelihood of detector saturation according to the present disclosure, a constant voltage may be provided at the x-ray tube insert throughout an entirety of a 3D scan. The constant voltage may be based on a size of the portion of the subject to be imaged (e.g., the size of the anatomy of the patient to be imaged). As one example, the voltage value may be determined via a pre-shot performed at a beginning of the 3D scan (e.g., immediately prior to acquisition of a first projection of an entire series of projections acquired during the 3D scan), where the pre-shot image may be identified as a reference image by the controller. For example, a thickness of the anatomy of a subject to be imaged may be different from subject to subject. By determining the constant voltage to be provided to the x-ray tube insert based on the thickness of the anatomy of a given subject to be imaged, image quality may be increased. Determining the constant voltage based on the pre-shot image may include, for example, determining the constant voltage as a function of a video level indicator (VLI) of the anatomy of the subject in the pre-shot image. The VLI may be a measure of a brightness of the anatomy of the subject in the pre-shot image. As one example, during conditions in which the VLI is lower, the controller may command a higher constant voltage to be provided to the x-ray tube insert throughout the scan of the subject, and during conditions in which the VLI is higher, the controller may command a lower constant voltage to be provided to the x-ray tube insert throughout the scan of the subject. The constant voltage may be determined via a lookup table stored in a memory of the controller. For example, the controller may calculate the constant voltage based on the VLI of the pre-shot image, where an input of the lookup table is the VLI and an output of the lookup table is the constant voltage. The constant voltage may be a function of the VLI, in some examples, with the controller calculating the constant voltage with the VLI as an input. Maintaining the voltage at the constant voltage may increase an ease of use of the imaging system in combination with the control routines described herein.

During conditions in which the voltage is maintained at a constant voltage, the electrical current is adjusted throughout the scan in order to provide adequate clarity of the imaged subject due to the different thicknesses of the anatomy of the subject. However, as described above, there may be a delay during conditions in which the electrical current provided to the x-ray tube insert 109 is adjusted from a first value to a second value during imaging of the subject.

During operation of conventional C-arm imaging systems, adjusting the electrical current from an initial value to a target value includes commanding the electrical current to the target value and waiting for a duration to transition from the initial value to the target value. The duration, or delay, may be relatively long as compared to a duration to transition the voltage from an initial voltage to a target voltage. The delay may result in an undesirably long response time of the conventional imaging system during conditions in which the electrical current is frequently adjusted (e.g., during a scan). As one example, the electrical current may be commanded (e.g., set) to a target electrical current, and during a scan of a subject, it may be desirable to transition the electrical current from a first value (e.g., 2 mA) to the target electrical current (e.g., 3 mA) within a relatively short duration. However, during the transition, the rate of change of the electrical current may decrease as the electrical current approaches the target current (e.g., the rate of change may decay exponentially as the electrical current approaches the target current). As a result, the duration of the transition may be significantly longer than a desired (e.g., commanded) transition time (e.g., the desired transition time may be 100 milliseconds, and the actual transition time may be 600 milliseconds). As a result, a duration of the scan may be increased and/or an imaging quality of the system may be decreased.

However, according to the present disclosure, the electronic controller 120 may command the electrical current to a corrected electrical current (e.g., a corrected value of the electrical current, determined by the controller) in order to transition the actual electrical current provided to the x-ray tube insert 109 from a first value (e.g., initial value) to a second value (e.g., target value) with a shorter transition duration. The corrected electrical current may be determined (e.g., calculated) by the controller via a function or lookup table stored in a memory of the controller, and by commanding the electrical current to the corrected electrical current, the speed of adjustment of the electrical current may be increased. As one example, according to the present disclosure, the transition duration between the first value and the second value may be within a range of 10%-15% of a transition duration of conventional imaging systems. As a result, an imaging performance of the imaging system may be increased. For example, in conventional imaging systems, a length of the transition duration may be sufficiently large such that adjusting the electrical current provided to the x-ray tube insert during a scan of the subject may be impractical (e.g., the long transition duration may lead to longer scan times, image aberrations or artifacts resulting from breathing or other movements of the subject throughout the longer scan times, etc.).

By controlling operation of the imaging system as described herein, the electrical current provided to the x-ray tube insert may be more readily adjusted during a scan of the subject (e.g., a speed of adjusting the electrical current may be increased). As a result, imaging quality may be increased. For example, by controlling the imaging system as described herein, the electrical current provided at the x-ray tube insert may be more quickly adjusted to compensate for variation in the thickness of the imaged anatomy for each projection of the scan (e.g., the electrical current may be adjusted from each projection to the respective, next projection).

Figure 2:
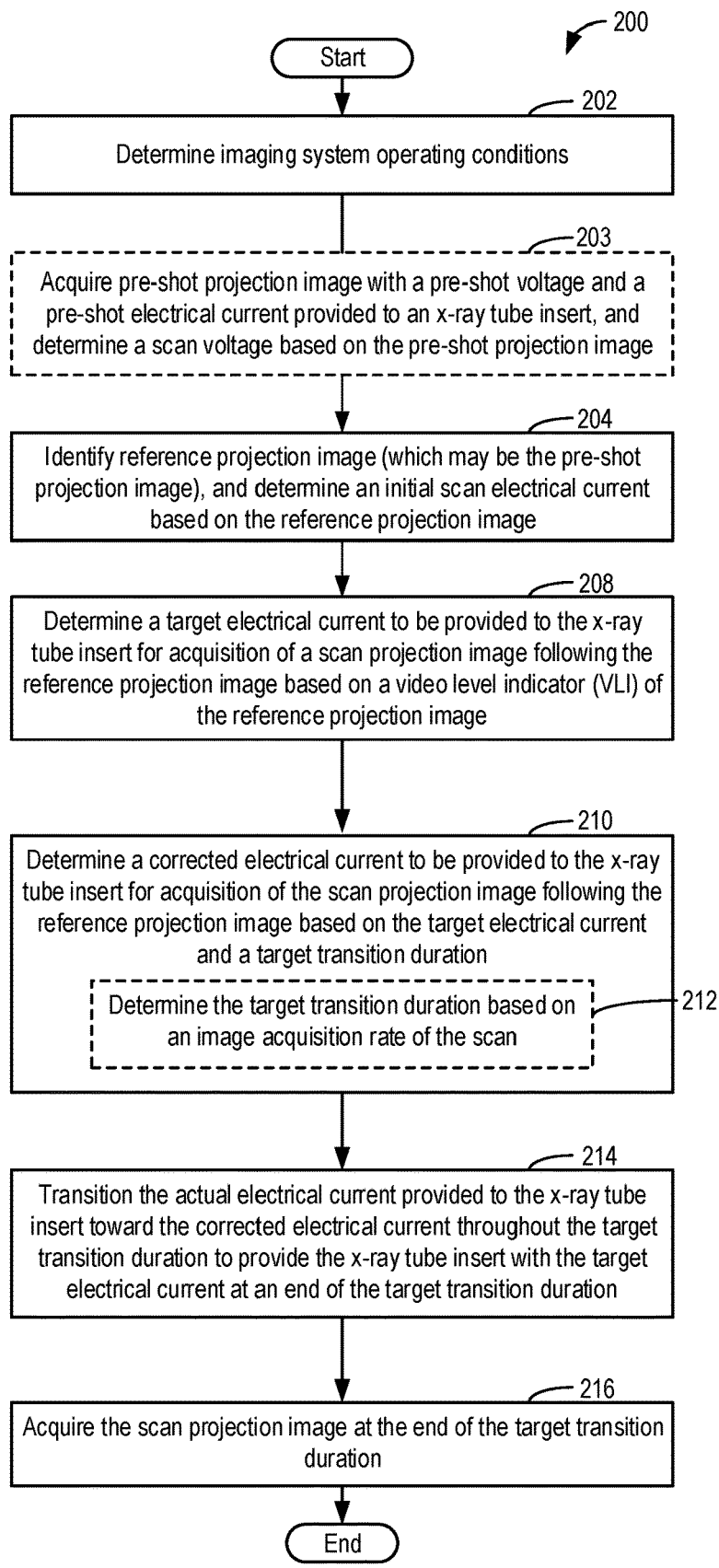
FIG. 2 shows a flowchart illustrating a method for controlling an x-ray tube of a medical imaging system, according to an embodiment.

Referring to FIG. 2, a flowchart is shown illustrating a method 200 (which may be referred to herein as an imaging method) for controlling an x-ray tube of a medical imaging system. The x-ray tube and medical imaging system may be similar to, or the same as, the x-ray tube 108 and the imaging system 100, respectively, described above with reference to FIG. 1. Controlling operation of the x-ray tube includes controlling operation of an x-ray tube insert housed within the x-ray tube. For example, as described herein, adjusting the electrical current provided to the x-ray tube refers to adjusting the electrical current provided to the x-ray tube insert. The x-ray tube insert may be similar to, or the same as, the x-ray tube insert 109 described above with reference to FIG. 1. Instructions for carrying out method 200 of the methods included herein may be executed by a controller (e.g., electronic controller 120 described above with reference to FIG. 1) based on instructions stored on a memory of the controller and in conjunction with signals received from sensors of the imaging system, such as the detector 130 described above with reference to FIG. 1. The controller may adjust imaging parameters to adjust imaging system operation (e.g., operation of the x-ray tube insert), according to the methods described below.

At 202 the method includes determining imaging system operating conditions. Determining imaging system operating conditions may include, for example, determining a value of actual electrical current at the x-ray tube insert, determining an actual voltage at the x-ray tube insert, determining a target scan range of the imaging system (e.g., determining a targeted amount of angle through which a C-arm of the imaging system rotates during a scan of a subject), determining an image acquisition rate of the imaging system, etc. As one example, an operator of the imaging system (e.g., a clinician) may input a target scan range of the imaging system prior to initiation of a scan of a subject based on an anatomy of the subject to be imaged by the imaging system (e.g., a torso of the subject), and the determination at 202 may include determining an amount of angle to be spanned by the C-arm of the imaging system during the scan (e.g., an amount of rotation of the C-arm around the imaging isocenter, such as 100 degrees, 150 degrees, 190 degrees, etc.).

The method optionally continues from 202 to 203, where the method includes acquiring a pre-shot projection image with a pre-shot voltage and a pre-shot electrical current provided to an x-ray tube insert, and determining a scan voltage based on the pre-shot image. Acquiring the pre-shot projection image may occur during conditions in which acquisition of projection images by the imaging system for a scan has not yet occurred. For example, an operator of the imaging system may input a command to the controller of the imaging system to indicate that scanning of a subject is desired, and as a result, the imaging system may acquire the pre-shot projection image as a single, initial projection image of the subject using the pre-shot voltage and the pre-shot electrical current provided to the x-ray tube insert. The pre-shot voltage may be a pre-determined, default voltage and the pre-shot electrical current may be a pre-determined, default electrical current, where the values of the pre-shot voltage and the pre-shot electrical current are stored in a memory of the controller. As one non-limiting example, the pre-shot voltage may be 100 kVp and the pre-shot electrical current may be 10 mA.

Determining the scan voltage based on the pre-shot image may include calculating the scan voltage as a function of the pre-shot voltage, the pre-shot electrical current, and/or a video level indicator (VLI) of the pre-shot image. For example, the scan voltage may be determined by the conversion of the VLI value to a scan voltage value via a lookup table stored in the memory (e.g., non-transitory memory) of the controller, as described above. The VLI of the pre-shot image may be a measurement of a brightness of the pre-shot image, and may include an average brightness of the pre-shot image in a region of interest (also referred to herein as a region of interact), such as a region of the image that corresponds to a center of the detector and/or a center of the subject in the pre-shot image.

The method continues from 202 or 203 to 204, where the method includes identifying a reference projection image, and determining an initial scan electrical current based on the reference projection image. The reference projection image is a projection image acquired by the imaging system. As one example, the reference projection image may be the pre-shot image described above. For example, during conditions in which the pre-shot image has been acquired by the imaging system and a first projection image included in a scan of the subject has not yet been acquired, the imaging system may identify the pre-shot image as the reference image. As another example, during conditions in which a scan of the subject is in progress and at least one projection image following the pre-shot projection image during the scan has been acquired by the imaging system, the reference image may be the most recently-acquired projection image (e.g., where, during conditions in which the pre-shot image is the only projection image that has been acquired by the imaging system in a scan of the subject, the pre-shot image is the most recently-acquired projection image identified as the reference image). The scan of the subject may be defined by a sequence of projection images (e.g., a series of sequential projection images) acquired by the imaging system. The projection images in the order of the sequence may be referred to herein as sequential images.

During conditions in which the reference projection image is the pre-shot projection image (e.g., the pre-shot image has been acquired and other projection images of the scan have not yet been acquired), the initial scan electrical current may be the pre-shot electrical current. During other conditions in which multiple projection images have been acquired during the scan, the initial scan electrical current may be the most recent actual electrical current provided at the x-ray tube insert (e.g., the actual electrical current provided at the x-ray tube insert at the time of acquisition of the most recently-acquired projection image).

The electrical current may be a function of the filament temperature, where the filament temperature and the electrical current vary with time (e.g., the filament temperature may vary according to a first order time function, and the current may be a function of the filament temperature). The filament temperature determines the number of free electrons in the filament (e.g., electrons that overcome the binding energy of the nuclei of atoms forming the filament). The voltage provided to the x-ray tube insert determines the number of free electrons reaching the anode of the x-ray tube insert (e.g., a percentage of the total free electrons of the filament that pass to the anode). The electrons of an individual atom of the filament have different binding energy levels, with each binding energy level of the atom including a number of electrons. During conditions in which the filament temperature increases, the energy of a first group of electrons at a first binding energy level may increase such that the first group of electrons becomes unbound from the atom (e.g., free electrons). During conditions in which the filament temperature increases even further, the energy of a second group of electrons at a second binding energy level may increase such that the second group of electrons becomes unbound from the atom (e.g., where the bond between the second group of electrons and the nucleus is stronger than the bond between the first group of electrons and the nucleus). Thus, the total number of free electrons may be based on the temperature of the filament, and the number of free electrons reaching the anode of the x-ray tube insert may be based on the voltage provided to the x-ray tube insert.

The number of free electrons reaching the anode may be further increased by increasing the electrical current provided to the x-ray tube insert or decreased by decreasing the electrical current provided to the x-ray tube insert. During conditions in which the filament temperature is lower (e.g., 900 degrees Celsius), an increase to the amount of electrical current provided to the x-ray tube insert (e.g., increasing the electrical current from 2 mA to 3 mA) may result in a lower amount of electrons passing to the anode, which may result in a lower intensity of x-ray radiation emitted by the x-ray tube insert. During conditions in which the filament temperature is higher (e.g., 1000 degrees Celsius), the same increase to the amount of electrical current provided to the x-ray tube insert may result in a higher amount of electrons passing to the anode and a higher intensity of the x-ray radiation emitted by the x-ray tube insert. Thus, the electrical current provided to the x-ray tube insert may be controlled based on the filament temperature to provide sufficient intensity of the x-ray radiation emitted by the x-ray tube insert.

The method continues from 204 to 208 where the method includes determining a target electrical current to be provided to the x-ray tube insert for acquisition of a scan projection image following the reference projection image based on a video level indicator (VLI) of the reference projection image. The scan projection image is a projection image immediately following the reference projection image in a sequence of the scan (e.g., in the sequence of projection images of the scan, the scan projection image is ordered immediately after the reference projection image in an order of the sequence). The target electrical current may be an electrical current determined by the controller to provide the scan projection image with a desired (e.g., targeted) VLI. For example, the target VLI may have a value associated with an optimized exposure of the scan projection image (e.g., an exposure that results in sufficient clarity of the subject imaged by the imaging system for analysis, diagnosis of the subject, etc., without exceeding a maximum saturation level of the detector).

The target electrical current associated with the scan projection image is based on the VLI of the reference projection image, where the VLI of the reference projection image is defined as the average value of the square-root encoded reference projection image in a given region of interact (ROI). For example, the target current for the scan projection image immediately following the reference projection image may be related to the VLI of the reference projection image by the relationships $VLI(k) = K_{VLI}\sqrt{mA(k)}$ and $$K_{VLI} = \frac{VLI(k)}{\sqrt{mA(k)}},$$

where VLI(k) is the VLI value of the reference projection image (where the reference projection image has a projection image number k in the order of the image sequence of the scan), mA(k) is the corresponding electrical current that was provided at the x-ray tube insert during acquisition of the reference projection image, $K_{VLI}$ is a proportionality coefficient, and VLI(k) is proportional to the square-root of mA(k).

To configure the scan projection image immediately following the reference projection image to have the target video level indicator (VLI) $VLI_T$, the target electrical current of the projection image immediately following the reference projection image is calculated via the relationship $$mA(k+1) = \left(\frac{VLI_T}{K_{VLI}}\right)^2.$$

The projection image number of the scan projection image is represented by (k+1), where k is the projection image number of the reference projection image as described above. By substituting $$K_{VLI} = \frac{VLI(k)}{\sqrt{mA(k)}},$$

the relationship becomes $$mA(k+1) = \left(\frac{VLI_T}{VLI(k)}\right)^2 \times mA(k).$$

The $VLI_T$ may be determined (e.g., selected) to provide a clinically relevant image projection quality (e.g., to provide an image contrast suitable for analysis of the anatomy of the subject by the clinician, diagnosis of the subject, etc.). The expression mA(k+1) is the target electrical current for the scan projection image immediately following the reference projection image and is expressed as mA(t) in the relationships $mA(t) = mA_0 + \sum_{n=1}^{N} a_n(mA_0, \delta mA) \times t^n$ and $mA(t) = mA_0 + (mA_c - mA_0)(1 - e^{-t/T_{mA}})$ described further below.

The method continues from 208 to 210 where the method includes determining a corrected electrical current to be provided to the x-ray tube insert for acquisition of the scan projection image following the reference projection image based on the target electrical current and a target transition duration. The controller may determine the corrected electrical current using a lookup table or function stored in the memory of the controller. For example, the corrected electrical current may be a function of the target electrical current and the target transition duration. As one example according to the present disclosure, the target (e.g., desired) electrical current at the x-ray tube insert as a function of time may vary according to the relationship $mA(t) = mA_0 + (mA_c - mA_0)(1 - e^{-t/T_{mA}})$, where $mA_0$ is the initial scan electrical current (e.g., actual measured electrical current) at time t=0, $T_{mA}$ is the corrected electrical current (e.g., commanded electrical current) at the time t=0, $T_{mA}$ is the x-ray tube electrical current time constant, and mA(t) is the target electrical current at time instant t. The electrical current time constant may have a pre-determined value stored in the memory of the controller and may be different for different x-ray tube inserts (e.g., the time constant may differ for different x-ray tube inserts depending on x-ray tube insert geometry, materials, etc.). By solving for the corrected electrical current $mA_c$, the relationship may be expressed as $$mA_c = \frac{mA(t) - mA_0 e^{-t/T_{mA}}}{1 - e^{-t/T_{mA}}}.$$

In order to calculate the corrected electrical current $mA_c$ used to provide the target electrical current at the x-ray tube insert in the target transition duration, the time t may be set to the target transition duration (e.g., 100 milliseconds, 33 milliseconds, 7 milliseconds, etc.) and the target electrical current mA(t) may be set to the desired value (e.g., a value determined by the controller based on the VLI of the reference image as described above). The controller $mA_c$ may then command the electrical current to the corrected electrical current to adjust the system to the target electrical current within the target transition duration, as described below. As another example according to the present disclosure, the target electrical current at the x-ray tube insert as a function of time may vary according to the relationship $mA(t) = mA_0 + \sum_{n=1}^{N} a_n(mA_0, \delta mA) \times t^n$, where mA(t) is the target electrical current at time t, and $a_n(mA_0, \delta mA)$ is a coefficient based on an initial electrical current $mA_0$ and a difference $\delta mA$ between the initial electrical current and the corrected electrical current at time t=0. The cost function $f(\delta mA) = mA(t) - mA_0 - \sum_{n=1}^{N} a_n(mA_0, \delta mA) \times t^n$ may be resolved in order to calculate the corrected electrical current $mA_c$.

The method at 210 may optionally include, at 212, determining the target transition duration based on an image acquisition rate of the scan. For example, the image acquisition rate may be based on number of projection images of the scan, and/or duration of the scan. As one example, during conditions in which the duration of the scan is 30 seconds and the total number of projection images to be included in the scan (e.g., to be acquired by the imaging system during the scan) is 300, the image acquisition rate may be ten projection images per second (e.g., one projection image per one-tenth of a second). The target transition duration during such conditions may be one-tenth of a second (100 milliseconds). The target transition duration may be a commanded duration based on the rotational speed of the C-arm and the scan range. For example, during conditions in which the scan range is 200 degrees around the subject (e.g., 200 degrees of rotation of the C-arm of the imaging system around the subject), the desired number of projections to be acquired during the scan is one projection per degree, and the desired rotational speed (e.g., angular velocity) of the C-arm is 5 degrees per second, the system may acquire 200 images in 40 seconds. The image acquisition rate during such conditions may be five projection images per second (e.g., one projection per one-fifth of a second). The target transition duration during such conditions may be one-fifth of a second (200 milliseconds). Other transition durations are possible.

The method continues from 210 to 214 where the method includes transitioning the actual electrical current provided to the x-ray tube insert toward the corrected electrical current throughout the target transition duration to provide the x-ray tube insert with the target electrical current at an end of the target transition duration. In particular, the controller controls the actual electrical current provided to the x-ray tube insert by commanding the electrical current to the corrected electrical current. Because the controller determines that commanding the electrical current to the corrected electrical current will result in the actual electrical current reaching the target electrical current once the target transition duration has elapsed (e.g., the controller commands the target transition duration to elapse between acquisition of sequential images of the subject during a scan by the imaging system, where acquisition of a given image and acquisition of another image immediately following the given image is spaced apart by the commanded target transition duration), the controller provides the target electrical current at the x-ray tube insert at the end of the target transition duration.

The method continues from 214 to 216 where the method includes acquiring the scan projection image at the end of the target transition duration. Acquiring the scan projection image may include emitting x-ray radiation from the x-ray tube insert through the subject to be imaged, and receiving attenuated x-ray radiation at the detector. The controller may generate the scan projection image based on the attenuated x-ray radiation received by the detector. The scan projection image is acquired at the end of the transition duration, such that the actual electrical current provided at the x-ray tube insert equals the target electrical current described above (e.g., the target electrical current determined at 208).

As described above, commanding the electrical current to the target electrical current may result in the actual electrical current provided at the x-ray tube insert to be different as compared to the target electrical current once the target transition duration has elapsed due to a delay associated with transitioning the electrical current to the target electrical current having a desired value (e.g., due to a slow response time of adjusting the electrical current to the target electrical current during conditions in which the electrical current is commanded directly to the target electrical current). However, by commanding the electrical current to the corrected electrical current, the controller ensures that the actual electrical current is approximately equal to the target electrical current at the end of the target transition duration.

Thus, by over-commanding the electrical current to the corrected electrical current rather than the target electrical current, the controller is able to control the actual electrical current to the target electrical current in a relatively short duration (e.g., the target transition duration) relative to conventional imaging systems. Examples of controlling the actual electrical current by commanding the electrical current to the corrected electrical current are described below with reference to FIGS. 3-5.

Because the electrical current may be quickly adjusted by controlling the electrical current according to the present disclosure, the imaging acquisition rate may be increased which may increase a speed of the scan of the subject. Increasing the speed of the scan may result in a lower likelihood of image artifacts or aberrations caused by movement of the subject during the scan (e.g., breathing, or other voluntary or involuntary movements). As a result, image quality may be increased. Further, because the electrical current may be quickly adjusted, the voltage provided to the x-ray tube insert may be maintained at a constant voltage (e.g., a voltage having a constant value), which may increase an ease of imaging of the subject and/or reduce a likelihood of oversaturation of the detector. For example, the voltage may be maintained at the determined scan voltage throughout an entire duration of the scan (e.g., the same, constant voltage may be commanded throughout the entire duration of the scan and the commanded voltage may not change throughout the scan). The voltage at the x-ray tube may be the determined scan voltage during acquisition of each image of a scan of the subject (e.g., x-ray radiation may be emitted by the x-ray tube while the commanded voltage of the x-ray tube is held at the same determined scan voltage for each image in an entire image sequence of the scan). In particular, "constant" voltage as described herein refers to less than 2% variation of the value of the voltage over the entire duration of the scan. As a result, portions of the anatomy of the subject having different thicknesses may be imaged with increased clarity by maintaining the voltage at the constant voltage and adjusting the electrical current as described above.

Referring to FIG. 3, graph 300 is shown. Graph 300 includes plot 304 showing an actual (e.g., measured) electrical current provided to an x-ray tube insert of an imaging system by commanding the electrical current to a corrected electrical current, similar to the examples described above. The imaging system and x-ray tube insert may be similar to, or the same as, the imaging system 100 and x-ray tube insert 109, respectively, shown by FIG. 1 and described above. Graph 300 additionally includes plot 316 illustrating the value of the corrected electrical current commanded by controller of the imaging system, plot 306 illustrating the value of the target electrical current, and marker 314 arranged along plot 304 indicating the value of the actual electrical current at an end of a target transition duration (indicated by vertical axis 302 arranged at 100 milliseconds along the horizontal axis indicating time). Further, graph 300 includes plot 308 illustrating the value of the actual electrical current provided at the x-ray tube insert in a conventional imaging system during conditions in which the electrical current is commanded directly to the target electrical current (e.g., without commanding the electrical current to the corrected electrical current as described by the present disclosure). Marker 312 is arranged along plot 308 to indicate the value of the actual electrical current at the time indicated by vertical axis 302, where plot 304 and plot 308 each begin at 0 milliseconds.

As indicated by plot 308, during conditions in which a scan is performed via a conventional imaging system and the electrical current provided to the x-ray tube insert is commanded from the initial electrical current (2 milliamps in the example shown by FIG. 3) directly to the target electrical current (3 milliamps in the example shown by FIG. 3), the transition from the initial electrical current to the target electrical current may be relatively slow compared to an image acquisition rate of the imaging system. In the example shown, the image acquisition rate is one image per 100 milliseconds. At 0 seconds along the horizontal axis, the electrical current provided at the x-ray tube insert (e.g., the initial electrical current) in the conventional imaging system is commanded directly to the target electrical current. Because the image acquisition rate is one image per 100 milliseconds, a projection image may be acquired at 100 milliseconds along the horizontal axis (e.g., the time indicated by vertical axis 302). However, due to the relatively slow adjustment speed of the electrical current, at 100 milliseconds along the horizontal axis, the electrical current indicated by plot 308 has a value of approximately 2.35 milliamps. As a result, the actual electrical current provided at the x-ray tube insert does not reach the target electrical current prior to acquisition of the image at 100 milliseconds.

However, by controlling operation of the imaging system according to the present disclosure, the adjustment speed of the electrical current from the initial electrical current to the target electrical current is significantly increased. For example, plot 304 shows the electrical current provided at the x-ray tube insert during conditions in which the electrical current is commanded from the initial electrical current at 0 seconds to the corrected electrical current (indicated by plot 316). Because the corrected electrical current is higher than the target electrical current, the actual electrical current transitions faster (e.g., at a higher speed) from the initial electrical current toward the target electrical current compared to configurations in which the actual electrical current is commanded directly from the initial electrical current to the target electrical current. In particular, the actual electrical current transitions from the initial electrical current (2 milliamps in the example shown by FIG. 3) between the time at 0 seconds and the time at 100 milliseconds and reaches the target electrical current (3 milliamps in the example shown by FIG. 3) at 100 milliseconds as indicated by marker 314. The actual electrical current may transition logarithmically toward the corrected electrical current (e.g., a rate of change of the actual electrical current may be higher toward a beginning of the transition duration compared to a rate of change of the actual electrical current toward an end of the transition duration).

At 100 milliseconds, the imaging system acquires a projection image and may update the target electrical current based on the acquired projection image (e.g., by updating the reference image to identify the acquired projection image as the reference image, as described above with reference to FIG. 2, which may be referred to herein as the updated reference image). The controller may determine an updated corrected electrical current based on the updated target electrical current and may command the electrical current at 100 milliseconds to transition toward the updated corrected electrical current. By transitioning the electrical current toward the updated corrected electrical current, the actual electrical current may have the value of the updated target electrical current at the time of acquisition of the following projection image (e.g., at 200 milliseconds along the horizontal axis). Similar determinations may be made for each following projection image of the scan such that the actual electrical current provided at the x-ray tube insert for acquisition of a given projection image is approximately equal to a target electrical current associated with the given projection image.

Referring to FIG. 4, another graph 400 is shown. Graph 400 includes plot 404 showing an actual (e.g., measured) electrical current provided to an x-ray tube insert of an imaging system by commanding the electrical current to a corrected electrical current, similar to the examples described above. The imaging system and x-ray tube insert may be similar to, or the same as, the imaging system 100 and x-ray tube insert 109, respectively, shown by FIG. 1 and described above. Graph 400 additionally includes plot 416 illustrating the value of the corrected electrical current commanded by controller of the imaging system, plot 406 illustrating the value of the target electrical current, and marker 412 arranged along plot 404 indicating the value of the actual electrical current at an end of a target transition duration (indicated by vertical axis 402 arranged at 100 milliseconds along the horizontal axis indicating time). Further, graph 400 includes plot 408 illustrating the value of the actual electrical current provided at the x-ray tube insert in a conventional imaging system during conditions in which the electrical current is commanded directly to the target electrical current (e.g., without commanding the electrical current to the corrected electrical current as described by the present disclosure). Marker 414 is arranged along plot 408 to indicate the value of the actual electrical current at the time indicated by vertical axis 402, where plot 404 and plot 408 each begin at 0 milliseconds.

As indicated by plot 408, during conditions in which a scan is performed via a conventional imaging system and the electrical current provided to the x-ray tube insert is commanded from the initial electrical current (2 milliamps in the example shown by FIG. 4) directly to the target electrical current (1 milliamp in the example shown by FIG. 4), the transition from the initial electrical current to the target electrical current may be relatively slow compared to an image acquisition rate of the imaging system. In the example shown, the image acquisition rate is one image per 100 milliseconds. At 0 seconds along the horizontal axis, the electrical current provided at the x-ray tube insert (e.g., the initial electrical current) in the conventional imaging system is commanded directly to the target electrical current. Because the image acquisition rate is one image per 100 milliseconds, a projection image may be acquired at 100 milliseconds along the horizontal axis (e.g., the time indicated by vertical axis 402). However, due to the relatively slow adjustment speed of the electrical current, at 100 milliseconds along the horizontal axis, the electrical current indicated by plot 408 has a value of approximately 1.5 milliamps. As a result, the actual electrical current provided at the x-ray tube insert does not reach the target electrical current prior to acquisition of the image at 100 milliseconds.

However, by controlling operation of the imaging system according to the present disclosure, the adjustment speed of the electrical current from the initial electrical current to the target electrical current is significantly increased (e.g., similar to the example described above with reference to FIG. 3). For example, plot 404 shows the electrical current provided at the x-ray tube insert during conditions in which the electrical current is commanded from the initial electrical current at 0 seconds to the corrected electrical current (indicated by plot 416). Because the difference between the initial electrical current and the corrected electrical current is larger than the difference between the initial electrical current and the target electrical current, the initial electrical current transitions faster (e.g., at a higher speed) toward the target electrical current compared to configurations in which the initial electrical current is commanded directly to the target electrical current. In particular, the actual electrical current transitions from the initial electrical current between the time at 0 seconds and the time at 100 milliseconds and reaches the target electrical current (e.g., 1 milliamp in the example shown by FIG. 4) at 100 milliseconds as indicated by marker 412.

At 100 milliseconds, the imaging system acquires a projection image and may update the target electrical current based on the acquired projection image (e.g., by updating the reference image to identify the acquired projection image as the reference image, as described above with reference to FIG. 2, which may be referred to herein as the updated reference image). The controller may determine an updated corrected electrical current based on the updated target electrical current and may command the electrical current at 100 milliseconds to transition toward the updated corrected electrical current. By transitioning the electrical current toward the updated corrected electrical current, the actual electrical current may have the value of the updated target electrical current at the time of acquisition of the following projection image (e.g., at 200 milliseconds along the horizontal axis). Similar determinations may be made for each following projection image of the scan such that the actual electrical current provided at the x-ray tube insert for acquisition of a given projection image is approximately equal to a target electrical current associated with the given projection image.

In one example, the plot 304 shown by FIG. 3 and the plot 404 shown by FIG. 4 may be associated with different scans performed by the imaging system 100 (e.g., plot 304 shown by FIG. 3 may be illustrative of operating conditions during a first scan, and plot 404 may be illustrative of operating conditions during a different, second scan). In another example, the plot 304 and the plot 404 may be associated with a single scan performed by the imaging system (e.g., plot 304 may represent conditions during a first portion of the scan and plot 404 may represent conditions during a second portion of the scan, where the time of 0 seconds along the horizontal axis indicating time in graph 300 is relative to a start of the first portion and the time of 0 seconds along the horizontal axis indicating time in graph 400 is relative to a start of the second portion). Although the image acquisition rate is one image per 100 milliseconds in the examples shown by FIGS. 3-4, in other examples the image acquisition rate may be different (e.g., one image per 33.3 milliseconds, one image per 66.6 milliseconds, etc.).

During conditions in which the target electrical current is higher than the initial electrical current (e.g., the actual electrical current provided at the x-ray tube insert during initiation of the transition of the electrical current toward the target electrical current), the value of the corrected electrical current commanded by the controller of the imaging system is higher than the value of the target electrical current (e.g., the corrected electrical current as indicated by plot 316 of FIG. 3 is greater than both of the target electrical current as indicated by plot 306 and the initial current which is the actual electrical current provided at the x-ray tube at 0 seconds along the horizontal time axis). Further, during conditions in which the target electrical current is lower than the initial electrical current, the value of the corrected electrical current commanded by the controller of the imaging system is lower than the value of the target electrical current (e.g., the corrected electrical current as indicated by plot 416 of FIG. 4 is less than both of the target electrical current as indicated by plot 406 and the initial current which is the actual electrical current provided at the x-ray tube at 0 seconds along the horizontal time axis). In this configuration, an absolute value of a difference between the initial electrical current and the target electrical current is less than an absolute value of a difference between the initial electrical current and the corrected electrical current. As one example, as shown by FIG. 3, the absolute value of difference 301 between the initial electrical current and the target electrical current is less than the absolute value of difference 303 between the initial electrical current and the corrected electrical current. As another example, as shown by FIG. 4, the absolute value of difference 401 between the initial electrical current and the target electrical current is less than the absolute value of difference 403 between the initial electrical current and the corrected electrical current. During conditions in which the target electrical current is the same as the initial electrical current, the corrected electrical current may be the same as the target electrical current and the initial electrical current.

Referring to FIG. 5, a graph 500 is shown illustrating an electrical current provided to an x-ray tube (e.g., provided to an x-ray tube insert housed within the x-ray tube) of an imaging system, such as the C-arm imaging system 100 shown by FIG. 1 and described above. In particular, graph 500 includes plot 502 showing a target electrical current throughout an entire duration of a scan of a subject (e.g., similar to the target electrical current described above with reference to FIG. 2), and plot 504 drawn in broken lines shows an actual electrical current provided at the x-ray tube insert. The actual electrical current is controlled by a controller (e.g., controller 120 shown by FIG. 1 and described above) according to the method 200 shown by FIG. 2 and described above. In particular, the controller adjusts the actual electrical current to closely match the target electrical current by commanding the electrical current to a corrected electrical current, where the corrected electrical current may be a function of the target electrical current as described above with reference to FIG. 2. The x-ray tube and x-ray tube insert may be similar to, or the same as, the x-ray tube 108 and x-ray tube insert 109, respectively, shown by FIG. 1 and described above. The graph 500 is a working example that presents experimental results in an imaging system operated according to the methods described herein.

In one embodiment, a mobile c-arm system comprises: an x-ray tube generating a two-dimensional x-ray field based on the commanded kVp and mA; an x-ray detector converting a two-dimensional x-ray field into a two-dimensional digital image; a C-shape gantry rotating around an isocenter to produce projection images; a control mechanism commanding the x-ray tube to produce x-ray on each projection, where a constant kVp being applied on all projections during an 3D scan, where the kVp value varying as the anatomy size determined through a pre-shot taken at the beginning of the 3D scan, and an initial mA is determined with the same pre-shot as the kVp; an over-commanded mA being requested to the x-ray tube such that the desirable mA is achieved from projection to projection afterwards, where the over-commanded mA value being determined based on the tube mA model and the video level of the present projection image.

In one embodiment, a method of producing x-ray in a 3D scan of a mobile c-arm system comprises: determining an anatomy size dependent tube kVp value and an initial tube mA value for a 3D scan through pre-shot taken at the beginning of the scan; calculating the video level from a projection image within a region of interact; computing the desirable mA based on the targeted video level for the next projection; obtaining the commanding mA for the next projection based on the tube mA model.

The disclosure also provides support for an imaging system, comprising: a C-shaped gantry, an x-ray tube coupled to a first end of the C-shaped gantry, an x-ray detector coupled to a second end of the C-shaped gantry, opposite to the x-ray tube, and a controller with computer readable instructions stored on non-transitory memory that when executed, cause the controller to: identify a reference image, determine a target electrical current based on the reference image, determine a corrected electrical current based on the target electrical current, and transition an electrical current provided to the x-ray tube to the target electrical current by commanding the electrical current to the corrected electrical current while maintaining a constant voltage provided to the x-ray tube. In a first example of the system, determining the corrected electrical current based on the target electrical current includes calculating the corrected electrical current as a function of the target electrical current, where the corrected electrical current is less than both of the target electrical current and the electrical current provided to the x-ray tube or greater than both of the target electrical current and the electrical current provided to the x-ray tube. In a second example of the system, optionally including the first example, the system further comprises: computer readable instructions stored on the non-transitory memory that when executed, cause the controller to: acquire a series of images in a single scan of a subject while rotating the C-shaped gantry around the subject, and for each image in the series of images, as each image is acquired: identify a most recently-acquired image in the series of images as an updated reference image, determine an updated target electrical current based on the updated reference image, determine an updated corrected electrical current based on the updated target electrical current, and transition the electrical current provided to the x-ray tube to the updated target electrical current by commanding the electrical current to the updated corrected electrical current while maintaining the constant voltage provided to the x-ray tube. In a third example of the system, optionally including one or both of the first and second examples, the constant voltage is based on the reference image and is maintained for each image acquired throughout an entire duration of a scan performed by the imaging system. In a fourth example of the system, optionally including one or more or each of the first through third examples, the system further comprises: computer readable instructions stored on the non-transitory memory that when executed, cause the controller to: acquire an image of a subject by: first, performing the identifying of the reference image, then performing the determining of the target electrical current based on the reference image, then performing the determining of the corrected electrical current based on the target electrical current, then performing the transitioning the electrical current provided to the x-ray tube to the target electrical current by commanding the electrical current to the corrected electrical current while maintaining the constant voltage provided to the x-ray tube, then while maintaining the constant voltage provided to the x-ray tube and maintaining the electrical current provided to the x-ray tube at the target electrical current, emitting x-ray radiation from the x-ray tube and receiving attenuated x-ray radiation at the x-ray detector. In a fifth example of the system, optionally including one or more or each of the first through fourth examples, the corrected electrical current is a function of the target electrical current, the electrical current provided to the x-ray tube, and a commanded duration between acquisition of sequential images of a subject, and the target electrical current is a function of a video level indicator of the reference image and an initial electrical current provided to the x-ray tube during acquisition of the reference image. In a sixth example of the system, optionally including one or more or each of the first through fifth examples, the corrected electrical current is defined by: . The disclosure also provides support for wherein is the corrected electrical current, is the target electrical current at time , is an initial electrical current, and is a time constant of the x-ray tube. In a first example of the system, the target electrical current is defined by: wherein is the target electrical current at time , and is a coefficient based on an initial electrical current and a difference between the initial electrical current and the corrected electrical current at time=0. In a second example of the system, optionally including the first example, the target electrical current is defined by: wherein is the target electrical current, is a target video level indicator, is a video level indicator of the reference image, and is an initial electrical current.

The disclosure also provides support for a method for a C-arm imaging system, comprising: determining an initial electrical current provided to an x-ray tube during acquisition of a reference image, determining a video level of a region of interact within the reference image, determining a target electrical current to be provided to the x-ray tube based on the video level, determining a corrected electrical current based on the target electrical current, and adjusting an actual electrical current provided to the x-ray tube from the initial electrical current to the target electrical current by commanding the actual electrical current to the corrected electrical current. In a first example of the method, an absolute value of a difference between the initial electrical current and the target electrical current is less than an absolute value of a difference between the initial electrical current and the corrected electrical current. In a second example of the method, optionally including the first example, the video level of the region of interact is proportional to the initial electrical current. In a third example of the method, optionally including one or both of the first and second examples, the video level is defined by: wherein is the video level of the region of interact, is the initial electrical current, and is a proportionality coefficient. In a fourth example of the method, optionally including one or more or each of the first through third examples, the method further comprises: maintaining a scan voltage at a constant value throughout an entire duration of the adjustment of the actual electrical current from the initial electrical current to the target electrical current. In a fifth example of the method, optionally including one or more or each of the first through fourth examples, the method further comprises: determining an image acquisition rate of the C-arm imaging system based on a rotational speed of a C-arm of the C-arm imaging system, and determining a transition duration of the actual electrical current from the initial electrical current to the target electrical current based on the image acquisition rate. In a sixth example of the method, optionally including one or more or each of the first through fifth examples, the corrected electrical current is based on the transition duration.

The disclosure also provides support for an imaging method, comprising: identifying a reference projection image and determining an initial electrical current of an x-ray tube based on the reference projection image, determining a target electrical current to be provided to the x-ray tube based on a video level indicator (VLI) of the reference projection image, determining a corrected electrical current for a projection image immediately following the reference projection image in an image sequence of a scan based on the target electrical current, and adjusting an actual electrical current at the x-ray tube from the initial electrical current toward the corrected electrical current until the actual electrical current equals the target electrical current, then, acquiring the projection image while the actual electrical current equals the target electrical current. In a first example of the method, determining the corrected electrical current for the projection image based on the target electrical current includes determining a transition duration between the reference projection image and the projection image based on an image acquisition rate of the scan and adjusting the corrected electrical current based on the transition duration. In a second example of the method, optionally including the first example, a duration of the adjustment of the actual electrical current from the initial electrical current to the target electrical current is equal to the transition duration, and further comprising maintaining a constant voltage at the x-ray tube throughout the transition duration. In a third example of the method, optionally including one or both of the first and second examples, adjusting the actual electrical current toward the corrected electrical current includes increasing or decreasing the actual electrical current logarithmically toward the corrected electrical current, with the target electrical current being between the initial electrical current and the corrected electrical current.

As used herein, the term "approximately" is construed to mean plus or minus five percent of the range unless otherwise specified.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
a C-shaped gantry;
an x-ray tube coupled to a first end of the C-shaped gantry;
an x-ray detector coupled to a second end of the C-shaped gantry, opposite to the x-ray tube; and
a controller with computer readable instructions stored on non-transitory memory that when executed, cause the controller to:
identify a reference image;
determine a target electrical current based on the reference image;
determine a corrected electrical current based on the target electrical current; and
transition an electrical current provided to the x-ray tube to the target electrical current by commanding the electrical current to the corrected electrical current while maintaining a constant voltage provided to the x-ray tube.

2. The imaging system of claim 1, wherein determining the corrected electrical current based on the target electrical current includes calculating the corrected electrical current as a function of the target electrical current, where the corrected electrical current is less than both of the target electrical current and the electrical current provided to the x-ray tube or greater than both of the target electrical current and the electrical current provided to the x-ray tube.

3. The imaging system of claim 1, further comprising computer readable instructions stored on the non-transitory memory that when executed, cause the controller to:
acquire a series of images in a single scan of a subject while rotating the C-shaped gantry around the subject; and
for each image in the series of images, as each image is acquired:
identify a most recently-acquired image in the series of images as an updated reference image;
determine an updated target electrical current based on the updated reference image;
determine an updated corrected electrical current based on the updated target electrical current; and
transition the electrical current provided to the x-ray tube to the updated target electrical current by commanding the electrical current to the updated corrected electrical current while maintaining the constant voltage provided to the x-ray tube.

4. The imaging system of claim 1, wherein the constant voltage is based on the reference image and is maintained for each image acquired throughout an entire duration of a scan performed by the imaging system.

5. The imaging system of claim 1, further comprising computer readable instructions stored on the non-transitory memory that when executed, cause the controller to:
acquire an image of a subject by:
first, performing the identifying of the reference image; then
performing the determining of the target electrical current based on the reference image; then
performing the determining of the corrected electrical current based on the target electrical current; then
performing the transitioning the electrical current provided to the x-ray tube to the target electrical current by commanding the electrical current to the corrected electrical current while maintaining the constant voltage provided to the x-ray tube; then
while maintaining the constant voltage provided to the x-ray tube and maintaining the electrical current provided to the x-ray tube at the target electrical current, emitting x-ray radiation from the x-ray tube and receiving attenuated x-ray radiation at the x-ray detector.

6. The imaging system of claim 1, wherein the corrected electrical current is a function of the target electrical current, the electrical current provided to the x-ray tube, and a commanded duration between acquisition of sequential images of a subject; and the target electrical current is a function of a video level indicator of the reference image and an initial electrical current provided to the x-ray tube during acquisition of the reference image.

7. The imaging system of claim 1, wherein the corrected electrical current is defined by:

$$mA_c = \frac{mA(t) - mA_0 e^{-t/T_{mA}}}{1 - e^{-t/T_{mA}}}.$$

wherein $mA_c$ is the corrected electrical current, $mA(t)$ is the target electrical current at time t, $mA_0$ is an initial electrical current, and $T_{mA}$ is a time constant of the x-ray tube.

8. The imaging system of claim 1, wherein the target electrical current is defined by:

$$mA(t) = mA_0 + \Sigma_{n=1}^N a_n(mA_0, \delta mA) \times t^n$$

wherein $mA(t)$ is the target electrical current at time t, and $a_n(mA_0, \delta mA)$ is a coefficient based on an initial electrical current $mA_0$ and a difference $\delta mA$ between the initial electrical current and the corrected electrical current at time t=0.

9. The imaging system of claim 1, wherein the target electrical current is defined by:

$$mA(k+1) = \left(\frac{VLI_T}{VLI(k)}\right)^2 \times mA(k)$$

wherein $mA(k+1)$ is the target electrical current, $VLI_T$ is a target video level indicator, $VLI(k)$ is a video level indicator of the reference image, and $mA(k)$ is an initial electrical current.

10. A method for a C-arm imaging system, comprising:
determining an initial electrical current provided to an x-ray tube during acquisition of a reference image;
determining a video level of a region of interact within the reference image;
determining a target electrical current to be provided to the x-ray tube based on the video level;
determining a corrected electrical current based on the target electrical current; and
adjusting an actual electrical current provided to the x-ray tube from the initial electrical current to the target electrical current by commanding the actual electrical current to the corrected electrical current.

11. The method of claim 10, wherein an absolute value of a difference between the initial electrical current and the target electrical current is less than an absolute value of a difference between the initial electrical current and the corrected electrical current.

12. The method of claim 10, wherein the video level of the region of interact is proportional to the initial electrical current.

13. The method of claim 10, wherein the video level is defined by:

$$VLI(k) = K_{VLI}\sqrt{mA(k)}$$

wherein $VLI(k)$ is the video level of the region of interact, $mA(k)$ is the initial electrical current, and $K_{VLI}$ is a proportionality coefficient.

14. The method of claim 10, further comprising:
maintaining a scan voltage at a constant value throughout an entire duration of the adjustment of the actual electrical current from the initial electrical current to the target electrical current.

15. The method of claim 10, further comprising:
determining an image acquisition rate of the C-arm imaging system based on a rotational speed of a C-arm of the C-arm imaging system; and
determining a transition duration of the actual electrical current from the initial electrical current to the target electrical current based on the image acquisition rate.

16. The method of claim 15, wherein the corrected electrical current is based on the transition duration.

* * * * *